(12) United States Patent
White

(10) Patent No.: US 8,702,696 B2
(45) Date of Patent: *Apr. 22, 2014

(54) VARIABLE SIZE APPARATUS FOR SUPPORTING DIAGNOSTIC AND/OR THERAPEUTIC ELEMENTS IN CONTACT WITH TISSUE

(75) Inventor: Brad R. White, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1121 days.

This patent is subject to a terminal disclaimer.

(21) Appl. No.: 12/695,887

(22) Filed: Jan. 28, 2010

(65) Prior Publication Data

US 2010/0217074 A1    Aug. 26, 2010

Related U.S. Application Data

(63) Continuation of application No. 11/116,076, filed on Apr. 27, 2005, now Pat. No. 7,662,150.

(51) Int. Cl.
*A61B 18/14*    (2006.01)

(52) U.S. Cl.
USPC ............................................. 606/41; 607/116

(58) Field of Classification Search
USPC ......... 606/41, 48–50; 607/101, 102, 116, 122
See application file for complete search history.

(56) References Cited

U.S. PATENT DOCUMENTS

| | | | |
|---|---|---|---|
| 5,902,300 A | 5/1999 | Hahnen et al. | |
| 6,071,274 A | 6/2000 | Thompson et al. | |
| 6,241,754 B1 | 6/2001 | Swanson et al. | |
| 6,245,067 B1 | 6/2001 | Tu et al. | |
| 6,311,692 B1 | 11/2001 | Vaska et al. | |
| 6,325,797 B1 | 12/2001 | Stewart et al. | |
| 6,529,756 B1 | 3/2003 | Phan et al. | |
| 6,542,781 B1 | 4/2003 | Koblish et al. | |
| 6,544,262 B2 | 4/2003 | Fleischman | |
| 6,682,526 B1 * | 1/2004 | Jones et al. | 606/32 |
| 6,711,444 B2 | 3/2004 | Koblish | |
| 6,745,080 B2 | 6/2004 | Koblish | |
| 6,837,885 B2 | 1/2005 | Koblish et al. | |
| 6,917,834 B2 | 7/2005 | Koblish et al. | |
| 6,960,206 B2 | 11/2005 | Keane | |
| 6,964,660 B2 | 11/2005 | Maguire et al. | |
| 7,662,150 B2 | 2/2010 | White | |
| 2002/0087208 A1 | 7/2002 | Koblish et al. | |
| 2002/0177765 A1 | 11/2002 | Bowe et al. | |
| 2003/0060820 A1 | 3/2003 | Maguire et al. | |
| 2003/0093072 A1 * | 5/2003 | Friedman | 606/41 |
| 2004/0167509 A1 | 8/2004 | Taimisto | |
| 2005/0070887 A1 | 3/2005 | Taimisto et al. | |

FOREIGN PATENT DOCUMENTS

WO    WO-03/022167 A1    3/2003

OTHER PUBLICATIONS

PCT International Search Report dated Aug. 8, 2006 for Int. App. No. PCT/US2006/011653.

* cited by examiner

*Primary Examiner* — Michael Peffley
(74) *Attorney, Agent, or Firm* — Seager, Tufte & Wickhem, LLC

(57) ABSTRACT

A probe that facilitates the creation of circumferential lesions in body structures that may vary in size.

24 Claims, 3 Drawing Sheets

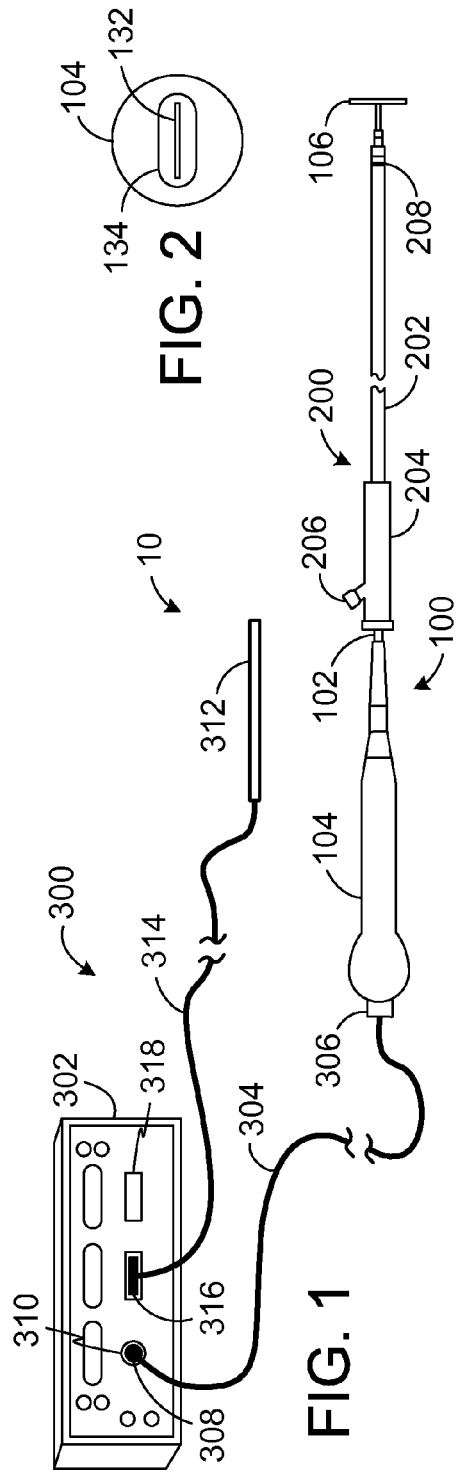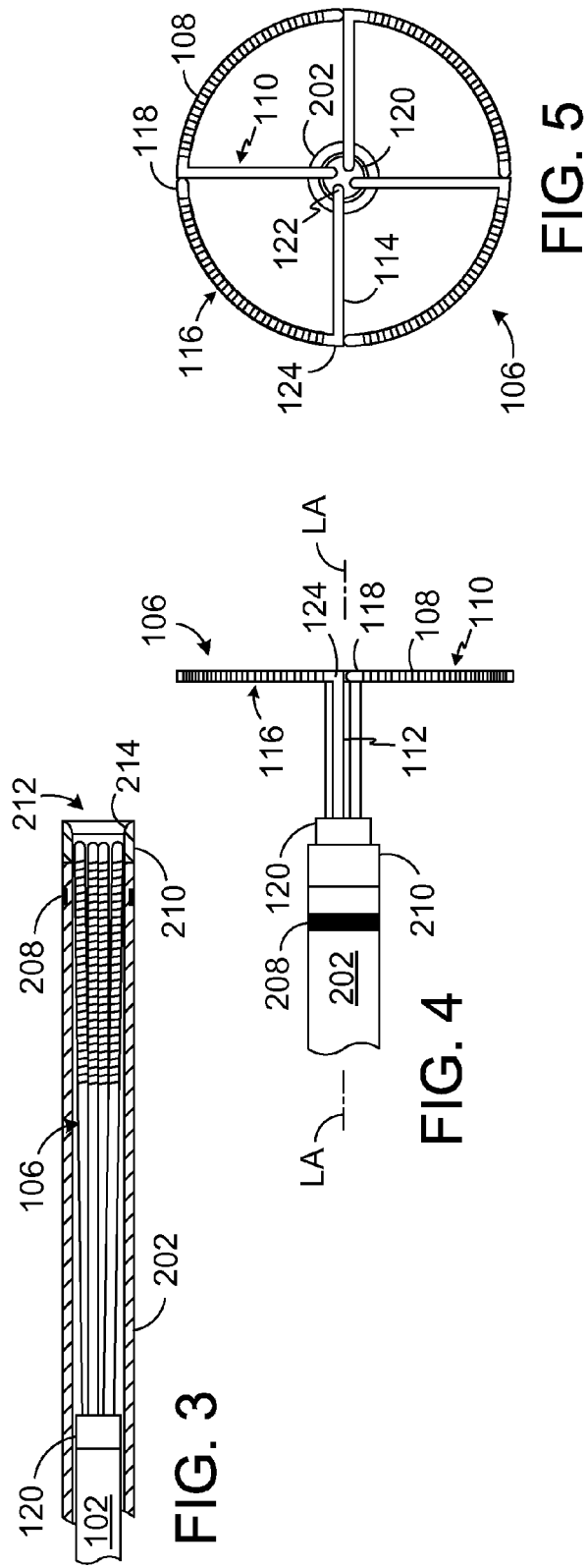

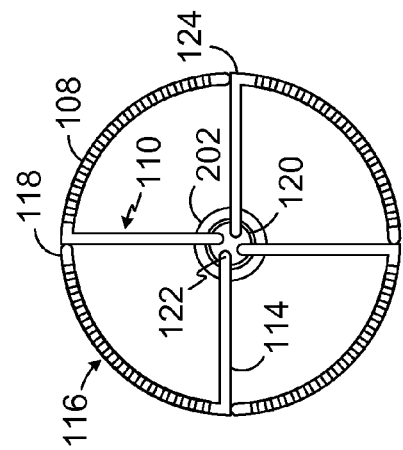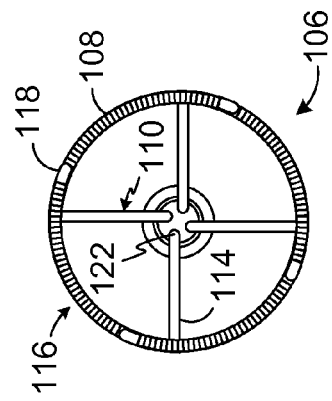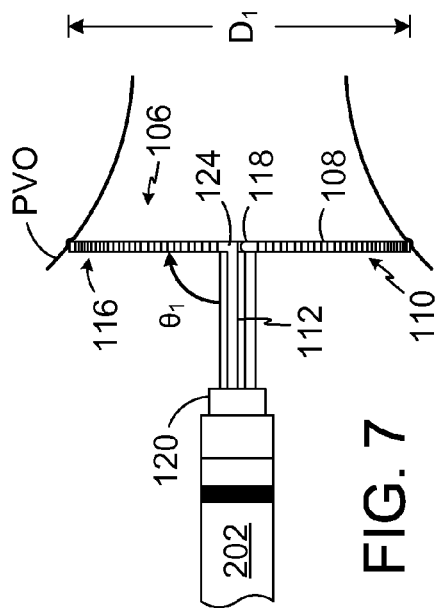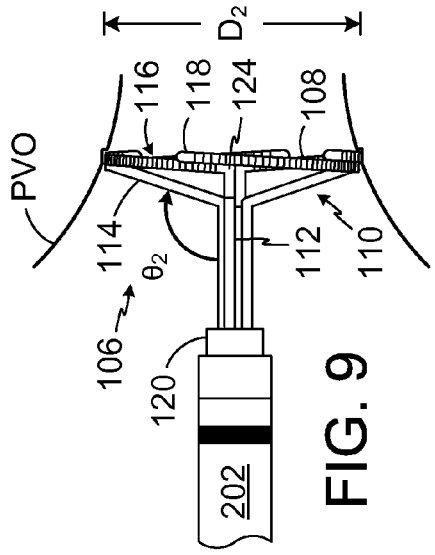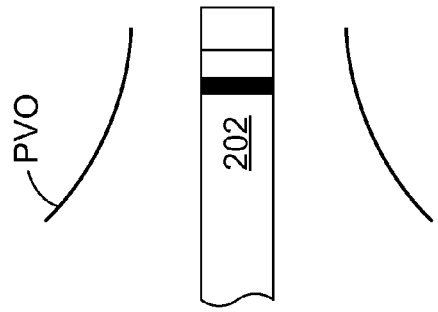

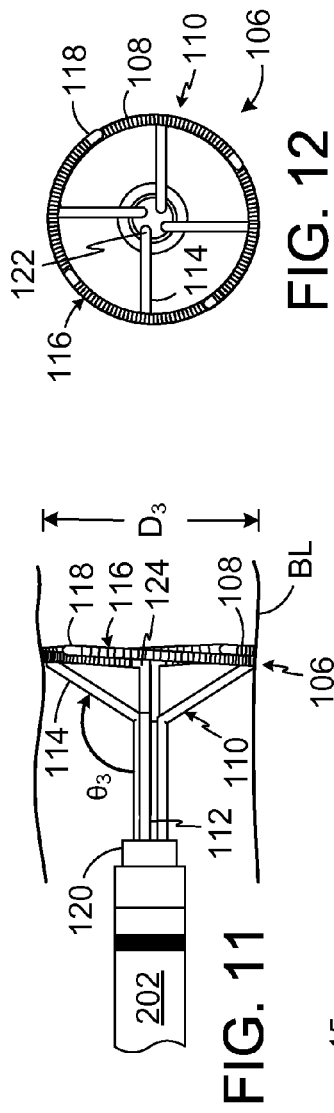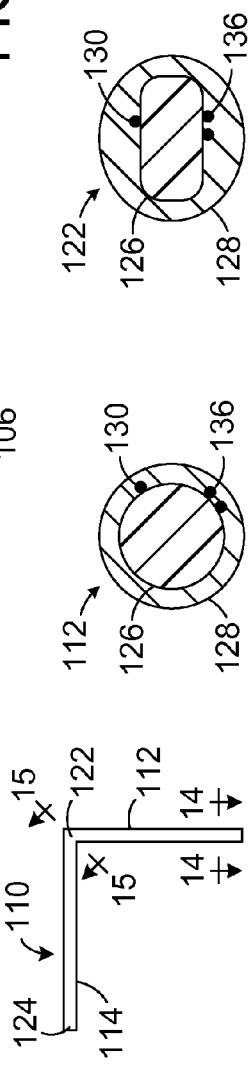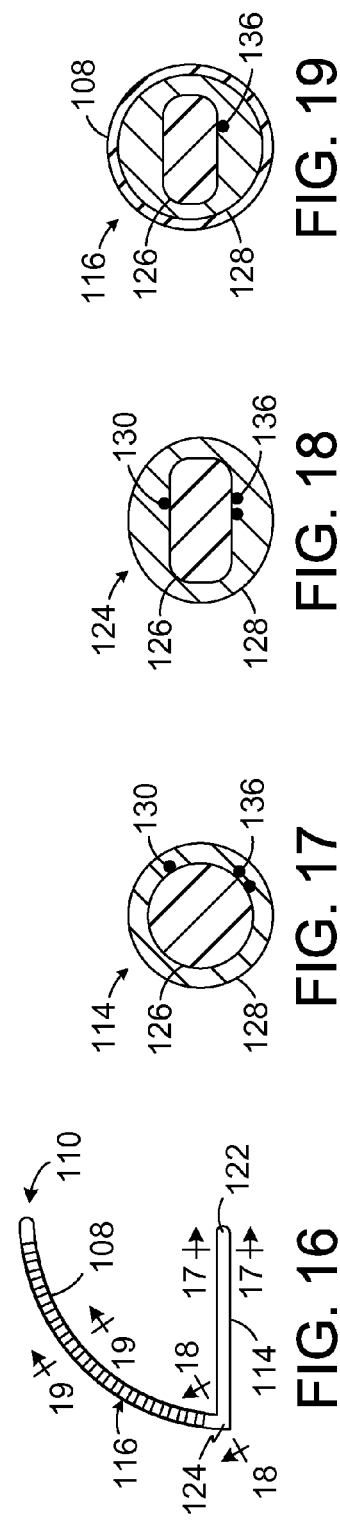

VARIABLE SIZE APPARATUS FOR SUPPORTING DIAGNOSTIC AND/OR THERAPEUTIC ELEMENTS IN CONTACT WITH TISSUE

CROSS-REFERENCE TO RELATED APPLICATION

This application is a continuation of application Ser. No. 11/116,076, filed Apr. 27, 2005, now U.S. Pat. No. 7,662,150.

BACKGROUND OF THE INVENTIONS

1. Field of Inventions

The present invention relates generally to medical devices that support one or more diagnostic and/or therapeutic elements in contact with body tissue associated with, for example, bodily orifices or lumens.

2. Description of the Related Art

There are many instances where diagnostic and/or therapeutic elements must be inserted into the body. For example, therapeutic elements may be used to form lesions to treat conditions in the heart, prostate, liver, brain, gall bladder, uterus, breasts, lungs and other solid organs. There are also many ways to form lesions. The application of electromagnetic radio frequency ("RF") energy to heat and eventually kill (i.e. "ablate") tissue is one method of forming a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue. The tissue coagulation energy is typically supplied and controlled by an electrosurgical unit ("ESU") during the therapeutic procedure. More specifically, after an electrophysiology or electrosurgical device has been connected to the ESU, and the electrodes or other energy transmission elements on the device have been positioned adjacent to the target tissue, energy from the ESU is transmitted through the electrodes to the tissue to from a lesion. The amount of power required to coagulate tissue ranges from 5 to 150 W.

With respect to the formation of therapeutic lesions in the heart to treat cardiac conditions such as atrial fibrillation, atrial flutter and arrhythmia, some procedures utilize catheters which form lesions on the endocardium in order to create a maze for electrical conduction similar to that created by surgical maze procedures. The lesions are carefully placed to interrupt the conduction routes of the most common reentry circuits.

Lesions within the heart may be formed by ablating tissue with one or more electrodes carried by a catheter. Catheters used to create lesions typically include a relatively long and relatively flexible shaft that carries the electrodes at or near its distal end. The proximal end of the catheter shaft is connected to a handle which may or may not include steering controls for manipulating the distal portion of the catheter shaft. The length and flexibility of the catheter shaft allow the catheter to be inserted into a main vein or artery (typically the femoral artery), directed into the interior of the heart where the electrodes contact the tissue that is to be ablated. Fluoroscopic imaging is used to provide the physician with a visual indication of the location of the catheter. Exemplary catheters are disclosed in U.S. Pat. Nos. 6,013,052, 6,203,525, 6,214,002 and 6,241,754.

More recently, surgical soft tissue coagulation probes that carry one or more electrodes on relatively short, stiff shafts have been developed. These probes may be used in endocardial and epicardial procedures where access to the heart is obtained by way of a thoracostomy, thoracotomy or median sternotomy. Such probes also allow endocardial lesions to be formed as a secondary procedure during a primary open heart surgical procedure such as mitral valve replacement, aortic valve replacement, and coronary artery bypass grafting. Exemplary surgical probes are disclosed in U.S. Pat. Nos. 6,142,994, 6,468,272 and 6,645,200.

One lesion that has proven to be difficult to form with conventional catheters and surgical probes (collectively referred to herein as "probes") is the circumferential lesion that is used to isolate a pulmonary vein and cure ectopic atrial fibrillation. Lesions that isolate a pulmonary vein may be formed in or around the pulmonary vein ostium or within the pulmonary vein itself. In some instances, these circumferential lesions are formed by dragging a tip electrode around the pulmonary vein or by creating a group of interconnected curvilinear lesions one-by-one around the pulmonary vein, both of which can be slow and/or leave gaps of conductive tissue after the procedure. It can also be difficult to achieve the adequate tissue contact with conventional catheters. In other instances, inflatable balloon-like devices that can be expanded within or adjacent to the pulmonary vein have been introduced. Although the balloon-like devices are generally useful for creating circumferential lesions, the inventors herein have determined that these devices have the undesirable effect of occluding blood flow through the pulmonary vein.

More recently, it has been proposed to provide probes with a pre-sized, continuous distal loop that positions a ring of electrodes transverse to probe shaft and around the target tissue structure when deployed. The present inventor has, however, determined that achieving the desired level of tissue contact with such a continuous loop can be dependent on the physician having accurate information concerning the size of the target structure so that the properly sized loop will be deployed. If the loop is too small, there will be insufficient tissue contact and, if the loop is too big, there is a risk of damage to the target structure.

SUMMARY OF THE INVENTION

A probe in accordance with one embodiment of a present invention includes a shaft and a variable size structure associated with the distal region of the shaft. In one implementation, electrodes are carried by the variable size structure. The variable size structure is configured such that it defines a predetermined shape. The size of the shape readily conforms to the size of the body structure into which it is deployed.

Such a probe provides a number of advantages over conventional apparatus. For example, the same variable size structure may be positioned within the body such that a ring of electrodes can be deployed in or around pulmonary veins or other body structures of varying size with an adequate level of electrode-tissue contact and without the risk of damage to the target structure. The variable size structure also defines an opening that allows blood or other bodily fluids to pass therethrough. As a result, the present probe also facilitates the formation of a circumferential lesion without the difficulties and occlusion of blood or other fluids that is associated with conventional apparatus.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 1 is a front view of an electrosurgical system including a probe in accordance with one embodiment of a present invention.

FIG. 2 is an end view of the probe illustrated in FIG. 1.

FIG. 3 is a partial section view showing the distal portion of the probe illustrated in FIG. 1 within a tubular member.

FIG. 4 is an enlarged side view of the distal portion of the probe illustrated in FIG. 1 in a relaxed state.

FIG. 5 is an enlarged end view of the distal portion of the probe illustrated in FIG. 1 in a relaxed state.

FIGS. 6 and 7 are side views showing the distal portion of the probe illustrated in FIG. 1 being deployed within a pulmonary vein ostium.

FIG. 8 is an end view of the distal portion of the probe illustrated in FIG. 1 in the orientation illustrated in FIG. 7.

FIG. 9 is a side view showing the distal portion of the probe illustrated in FIG. 1 deployed within a pulmonary vein ostium.

FIG. 10 is an end view of the distal portion of the probe illustrated in FIG. 1 in the orientation illustrated in FIG. 9.

FIG. 11 is a side view showing the distal portion of the probe illustrated in FIG. 1 deployed within a body lumen.

FIG. 12 is an end view of the distal portion of the probe illustrated in FIG. 1 in the orientation illustrated in FIG. 11.

FIG. 13 is a side view of a spline in accordance with one embodiment of a present invention.

FIG. 14 is a section view taken along line 14-14 in FIG. 13.
FIG. 15 is a section view taken along line 15-15 in FIG. 13.
FIG. 16 is an end view of the spline illustrated in FIG. 13.
FIG. 17 is a section view taken along line 17-17 in FIG. 16.
FIG. 18 is a section view taken along line 18-18 in FIG. 16.
FIG. 19 is a section view taken along line 19-19 in FIG. 16.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Introduction
II. Exemplary Probes
III. Electrodes, Temperature Sensing and Power Control The section titles and overall organization of the present detailed description are for the purpose of convenience only and are not intended to limit the present inventions.

I. Introduction

The present inventions may be used within body lumens, chambers or cavities for diagnostic and/or therapeutic purposes in those instances where access to interior bodily regions is obtained through, for example, the vascular system or alimentary canal and without complex invasive surgical procedures. For example, the inventions herein have application in the diagnosis and treatment of arrhythmia conditions within the heart. The inventions herein also have application in the diagnosis or treatment of ailments of the gastrointestinal tract, prostrate, brain, gall bladder, breasts, uterus, and other regions of the body. The structures are also adaptable for use with probes other than catheter-based probes. For example, the structures disclosed herein may be used in conjunction with surgical soft tissue coagulation probes.

II. Exemplary Probes

As illustrated for example in FIGS. 1-5, a catheter-based probe 100 in accordance with one embodiment of a present invention includes a hollow, flexible shaft 102. The proximal end of the shaft 102 is attached to a handle 104, while the distal end of the shaft supports a variable size structure 106 that carries a plurality of electrodes 108 or other operative elements. The variable size structure 106, which is capable of positioning the electrodes 108 in contact with tissue in or around body orifices, lumens and regions of varying size in the manner discussed in greater detail below, includes a plurality of splines 110. In the absence of a straightening or compressive force, the splines 110 will together assume a predetermined size and overall closed shape. If, however, the variable size structure 106 is deployed within a body structure that is smaller than the predetermined size, the variable size structure will assume a smaller version of the overall closed shape. As a result, the present probe can achieve the proper level of electrode/tissue contact in body orifices, lumens and regions of varying size. The variable size structure 106 also defines an open area interior to the electrodes 108 through which blood or other bodily fluids can flow. As a result, the variable size structure 106 can be used to create a circumferential lesion in or around the pulmonary vein, or other bodily orifice or lumen, without occluding fluid flow.

Although the present inventions are not limited to any particular shape, the electrode supporting portions of the splines 110 together assume closed circular shape in the exemplary embodiment illustrated in FIGS. 1-5. The overall shape will, of course, depend on the intended application. Other suitable shapes include, for example, elliptical shapes and kidney shapes. The shapes may also be symmetrical (as shown) or asymmetrical, depending on the intended application. Additionally, although the exemplary variable size structure 106 includes four splines 110, the number of splines may also be varied to suit particular applications. A variable size structure intended for use in a relatively small space may have fewer than four splines, while a variable size structure intended for use in a relatively large space may have more than four splines.

Referring more specifically to FIGS. 4 and 5, which show the variable size structure 106 in its pre-shaped and relaxed (i.e. unstressed) state, each of the splines 110 in the illustrated embodiment are essentially identical. The splines 110 include a distally extending section 112, an outwardly extending section 114, and an electrode support section 116 with a distal end 118. The distally extending section 112 is parallel to the shaft longitudinal axis LA. The electrode support section 116 is curved and defines an arc of 90 degrees. The electrode support section distal end 118 abuts or is close to, but is not fixedly secured to, the next adjacent spline. The proximal ends of the distally extending sections are mounted on a tip member 120 that is secured to the distal end of the shaft 102 in, for example, the manner described U.S. Pat. No. 6,544, 262, which is incorporated herein by reference. Thus, although the present inventions are not so limited, the proximally ends of the splines 110 are fixed in place with respect to the distal end of the shaft 102. The distally extending section 112 is connected to the outwardly extending section 114 by a joint 122, and the outwardly extending section is connected to the electrode support section 116 by a joint 124. Absent the application of force to the exemplary variable size structure 106, the joint 122 is a 90 degree joint and, accordingly, the outwardly extending section 114 is perpendicular to the shaft longitudinal axis LA. The joint 124 is a 90 degree joint about the longitudinal axis LA in the illustrated embodiment.

The configuration described above results in a variable size structure 106 with an overall electrode supporting portion (i.e. the combination of the four electrode support sections 116) that is generally circular in shape, defines a plane that is perpendicular to the shaft longitudinal axis LA, and is centered with respect to (i.e. coaxial with) the longitudinal axis. This aspect of the illustrated embodiment may also be varied to suit particular applications. For example, the electrode supporting portion of the variable size structure 106 may be tilted such that it defines a plane at an angle of between 45 degrees and 90 degrees with the longitudinal axis LA. The electrode supporting portion may also be off-center (i.e. non-coaxial) with the longitudinal axis LA. The joints 122 and 124 may also define angles other than 90 degrees, e.g. the joint 122 may define an angle greater than 90 degrees. The distally extending sections 112 could also be angled with respect to the longitudinal axis LA.

The distal end 118 in the exemplary embodiment is a "free distal end." As used herein, the term "free distal end" means that no pull wire or other similar control structure, which extends outwardly from the distal end and back to the proximal region of the shaft, is connected to the distal end 118.

Referring to FIG. 1, the exemplary probe 100 may be advanced though a conventional guide sheath device 200 to the target location. The exemplary guide sheath device 200 includes a tubular member 202 and a handle 204 with a fluid port 206. The tubular member 202 should be stiffer than the shaft 102 and variable size structure 106 and lubricious to reduce friction during movement of the probe 100. The tubular member 202 may also be provided with a radiopaque marker 208 and a relatively soft distal tip 210 to prevent tissue trauma. The exemplary guide sheath device 200 is non-steerable and may be advanced over a guide wire (not shown) to the target tissue region in conventional fashion. Once the distal end 212 has reached the target tissue region, the guide wire may be withdrawn so that the shaft 102 and variable size structure 106 may be inserted. Alternatively, a steerable guide sheath device may be provided. In either case, a sheath introducer (not shown), such as those used in combination with basket catheters, may be used when introducing the variable size structure 106 into the guide sheath device 200.

As illustrated in FIG. 3, each of the splines 110 in the exemplary variable size structure 106 will assume a generally straightened shape while they are within the tubular member 202. The splines 110 will, however, deflect as they advance through the vasculature. After the variable size structure 106 has reached the target tissue region, the tubular member 202 may be moved proximally until it is proximal to the variable size structure. The variable size structure 106 may, alternatively, be advanced distally out of the tubular member. Once free of the compressive, straightening forces associated with the tubular member 202, the variable size structure 106 will return to its pre-shaped state, which illustrated in FIGS. 4 and 5, so that the electrodes 108 may be positioned against the target tissue structure for the intended diagnostic and/or therapeutic procedure. Once the procedure is completed, the probe 100 may be withdrawn from the patient by way of the guide sheath device 200. To that end, the guide sheath distal tip 210 includes a bevel 214 to facilitate withdrawal of the variable size structure 106 back into the tubular member 202.

The joints 122 and 124 are more flexible than the distally extending section 112, outwardly extending section 114, and electrode support section 116. The electrode support section 116 is more flexible that the distally extending section 112 and the outwardly extending section 114. The relative flexibility of the joints 122 and 124 and electrode support section 116 allows the variable size structure 106 to assume sizes less than that illustrated in FIGS. 4 and 5, as is described below with reference to FIGS. 6-12. The joints 122 and 124 and electrode support section 116 may be made more flexible by, for example, reducing the thickness of certain portions of the joints and electrode support section, as compared to the remainder of the spline 110, in the manner described below with reference to FIGS. 13-19.

Turning first to FIGS. 6-8, one exemplary use of the probe 100 is the formation of therapeutic lesions in the pulmonary vein ostium (PVO). First, as illustrated in FIG. 6, the tubular member 202 and variable size structure 106 are advanced through the left atrium to a position within the PVO that will result in the desired positioning of the variable size structure when it is free of the tubular member. Next, the guide sheath device 200 is pulled proximally while the probe 100 is held in place so that the tubular member distal end 212 will be located proximal to the variable size structure 106. The variable size structure 106 will then be free to expand to the unstressed orientation illustrated in FIGS. 7-8. The electrode support sections 116 in the exemplary variable size structure 106 together define an overall circular shape with the distal ends 118 abutting the joints 124 of the adjacent splines 110. The size of the electrode supporting portion of the variable size structure 106 is represented herein by its diameter $D_1$. Other representations of size, such as perimeter or long/short axis dimensions, may be used in the context of non-circular electrode supporting portions and bodily environments.

In the exemplary deployment illustrated in FIG. 7, the portion of the PVO in contact with the variable size structure 106 has the same diameter D1 as the combined electrode support sections 116, which is why the variable size structure is not subject to compressive force and is in its relaxed state. The variable size structure 106 will, therefore, create an adequate level of contact between the electrodes 108 and the PVO tissue. It should also be noted that the angle $\theta_1$ that is defined by the spline distally extending section 112 and outwardly extending section 114, which are connected by the joint 122, is 90 degrees when the variable size structure is in its unstressed orientation.

FIGS. 9 and 10 show the exemplary variable size structure 106 after it has been expanded within a portion of the PVO that has a smaller diameter than the unstressed diameter $D_1$ illustrated in FIGS. 7 and 8. The compressive force applied by the PVO prevents the variable size structure 106 from expanding beyond diameter $D_2$, which is smaller than diameter $D_1$, when the variable size structure is deployed. Nevertheless, the flexibility of the joints 122 and 124 and electrode support section 116, and the fact that the electrode support section distal ends 118 are not connected to the adjacent splines 110, will allow the electrode supporting portion of the variable size structure 106 to assume an overall closed circular shape so that the electrodes 108 can be used to form a continuous circular lesion. The closed circular shape will simply be smaller (diameter $D_2$) than the unstressed closed circular shape (diameter $D_1$). The joint 124 on each spline 110 will deflect so that the angle $\theta_2$, which is defined by the distally extending section 112 and outwardly extending section 114, is greater than 90 degrees (as shown) or is less than 90 degrees in those instances where the outwardly extending sections deflect proximally. As a result, the distance between opposing joints 124, i.e. the diameter of the circular shape, will decrease. The electrode support sections 116 and joints 124 will bend to accommodate the reduction in diameter. However, because the length of the electrode support sections 116 remains the same, the distal ends 118 will extend circumferentially beyond the joints 124 of the adjacent splines 110 (FIG. 10) instead of abutting the joints (FIG. 8). This results in a slight overlap of the electrode support sections 116. The overlap, in turn, allows the electrode support sections 116 to form a smaller electrode supporting portion despite the fact that their individual lengths have not changed.

As illustrated for example in FIGS. 11 and 12, the variable size structure 106 may be been expanded within a body lumen BL with a diameter $D_3$ that is smaller than diameter $D_2$. Here too, the flexibility of the joints 122 and 124 and electrode support section 116 will allow the electrode supporting portion of the variable size structure 106 to assume an overall closed circular shape so that the electrodes 108 can be used to form a continuous lesion. Angle $\theta_3$, which is defined by the distally extending section 112 and outwardly extending section 114, will be greater than angle $\theta_2$ (as shown), or less than angle $\theta_2$ in those instances where the outwardly extending sections deflect in the proximal direction. As a result, the distance between opposing joints 124, i.e. the diameter of the circular shape, will further decrease as compared to the orientation illustrated in FIGS. 9 and 10, and the electrode support sections 116 and joints 124 will bend to accommodate the reduction in diameter. The distal ends 118 will also extend circumferentially further beyond the joints 124 of the adjacent splines 110, which results in a greater overlap of the electrode support sections 116 than is shown in FIG. 10.

Referring now to FIGS. 13-19, each of the splines 110 consists of a resilient inert wire 126 that is covered by an electrically nonconductive coating or sleeve 128. The cross-sectional shape of each portion of the wire 126 will depend on the function being performed by that portion of the wire. More specifically, and although the present inventions are not limited to the cross-sectional shapes in the illustrated embodiment, the wire 126 is generally circular in cross-sectional shape within the distally extending section 112 and the outwardly extending section 114 because these portions of the spline 110 are not intended bend during use. The sections of the wire 126 within the joints 122 and 124, which are intended to bend in a predetermined manner, have a generally rectangular cross-sectional shape. The rectangles should be oriented such that the long axis is perpendicular to the intended bend direction. The short axis is smaller than the diameter of the circular sections of the wire. Similarly, the section of the wire 126 within the electrode support section 116 is generally rectangular cross-sectional shape, with the long axis perpendicular to the intended bend direction, in order to insure that the electrode support portions bend in the manner sequentially illustrated in FIGS. 8, 10 and 12.

With respect to materials and dimensions, and although the present inventions are not limited to any particular materials and dimensions, the exemplary shaft 102 is formed from a biocompatible thermoplastic material, such as a PEBAX® material (polyether block emide) and stainless steel braid composite, which has good torque transmission properties. In some implementations, an elongate guide coil (not shown) may also be provided within the shaft 102. The exemplary shaft is also about 5 French to about 9 French in diameter and about 60 cm to 160 cm in length.

The overall dimensions of the variable size structure 106 will, of course, depend on the intended application. In the case of variable size structures intended for use within or around the pulmonary veins or pulmonary vein ostiums, the outer diameter of the variable size structure could range from about 1 cm to 3 cm when in its relaxed state, down to about 3 mm to 8 mm in its compressed state.

Turning to the splines 110, suitable materials for the spline wires 126 include nickel titanium (commercially available under the trade name nitinol) or 17-7 stainless steel that is heat set into the desired configuration. Resilient injection molded inert plastic may also be used. The thickness of the spline wires 126 is preferably between about 0.25 mm and about 0.5 mm. Another suitable wire material is actuator-type Nitinol that has a transition temperature above body temperature (typically between about 55° C. and 70° C.). When this material is heated to the transition temperature by, for example, supplying power to the electrodes 108, the internal structure of the material dynamically changes and causes the material to contract and assume its heat set shape. Additional information concerning shape memory alloys is provided in T. W. Duerig et al., "Actuator and Work Production Devices," *Engineering Aspects of Shape Memory Alloys*, pp. 181-194 (1990).

The electrically nonconductive coating or sleeve 128 is preferably a polymeric, electrically nonconductive material, such as polyethylene or polyurethane.

The present inventions also include steerable catheters. For example, the catheter 100 described above may be modified by adding one or more steering wires, a steering spring (or "center support") near the distal end of the shaft 102, and an actuator (such as a rotatable knob or piston) on the handle 104, in order to provide steering capability.

The present inventions also have application in the area of surgical probes. Surgical probes in accordance with the present inventions include a handle, a relatively short shaft, and the variable size structure 106 and electrodes 108 (or other operative elements) described above in the catheter context carried on the distal end of the shaft. Preferably, the length of the shaft is about 10 cm to 45 cm. The shaft is also preferably relatively stiff. In other words, the shaft is either rigid, malleable, or somewhat flexible. Exemplary surgical probes are disclosed in U.S. Pat. Nos. 6,142,994, 6,468,272 and 6,645,200, which are incorporated herein by reference. The surgical probe may be used in combination with a relatively short tubular member that may be moved proximally and distally relative to the variable size structure 106 so that the variable size structure may be deployed and withdrawn in the manner described above.

III. Electrodes, Temperature Sensing and Power Control

As noted above, the operative elements in the illustrated embodiment are the electrodes 108. However, other operative elements, such as lumens for chemical ablation, laser arrays, ultrasonic transducers, microwave electrodes, and ohmically heated hot wires, and such devices may be substituted for the electrodes.

The exemplary electrodes 108 are preferably in the form of wound, spiral coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. Exemplary coil electrodes are disclosed in U.S. Pat. Nos. 5,575,810 and 5,797,905.

As an alternative, the electrodes may be in the form of plurality of solid rings of conductive material, like platinum, spaced along the length of each electrode support section 116, or can comprise a conductive material, like platinum-iridium or gold, coated upon the electrode support portion using conventional coating techniques or an ion beam assisted deposition (IBAD) process. For better adherence, an undercoating of nickel or titanium can be applied. The electrodes can also be in the form of helical ribbons or a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks.

The electrodes 108 are preferably about 2 mm to about 8 mm in length. In the illustrated embodiment, the electrodes are 8 mm in length with about 0.5 mm to 1 mm spacing, which will result in the creation of continuous lesion patterns in tissue, i.e. lesion patters that extend from one electrode to another, when coagulation energy is applied simultaneously to adjacent electrodes.

The portion of the electrodes 108 that are not intended to contact tissue (and be exposed to the blood pool) may be masked through a variety of techniques with a material that is preferably electrically and thermally insulating. This prevents the transmission of coagulation energy directly into the blood pool and directs the energy directly toward and into the tissue. For example, a layer of UV adhesive (or another adhesive) may be painted on preselected portions of the electrodes to insulate the portions of the electrodes not intended to contact tissue. Deposition techniques may also be implemented to position a conductive surface only on those portions of the variable size structure 106 intended to contact tissue. Alternatively, a coating may be formed by dipping the electrodes in PTFE material.

The electrodes 108 are electrically coupled to individual wires 130 (see, for example, FIG. 14) that conduct coagulating energy to them. The wires 130 extend under the electrically nonconductive coating 128 and are then passed in conventional fashion through a lumen extending through the shaft 102 to an electrical connector 132 (e.g. a PC board, edge card connector, subminiature D connector, ribbon cable connector, or pin and socket connector) in the handle 104, which is illustrated in FIG. 2. The electrical connector 132 is accessible by way of a port 134.

A plurality of temperature sensors (not shown), such as thermocouples or thermistors, may be located on, under, abutting the longitudinal end edges of, or in between, the electrodes 108. Preferably, the temperature sensors are located at the longitudinal edges of the electrodes on the distally facing side of the variable size structure 106. In some embodiments, a reference thermocouple may also be provided. For temperature control purposes, signals from the temperature sensors are transmitted to the source of coagulation energy by way of wires 136 (FIG. 14) that are also connected to the aforementioned connector 132 in the handle 104.

Finally, the electrodes 108 may be covered with a porous material coating, which transmits coagulation energy through an electrified ionic medium. For example, as disclosed in U.S. Pat. No. 5,991,650, the electrodes 108 may be coated with regenerated cellulose, hydrogel or plastic having electrically conductive components. With respect to regenerated cellulose, the coating acts as a mechanical barrier between the probe components, such as the electrodes, preventing ingress of blood cells, infectious agents, such as viruses and bacteria, and large biological molecules such as proteins, while providing electrical contact to the human body. The regenerated cellulose coating also acts as a biocompatible barrier between the probe components and the human body, whereby the components can now be made from materials that are somewhat toxic (such as silver or copper). The porous material is saturated with ionic fluid (such as saline) prior to use.

Turning to FIG. 1, an exemplary electrophysiology system 10 includes the probe 100, guide sheath device 200 and a power supply and control apparatus 300. The power supply and control apparatus 300 includes an electrosurgical unit ("ESU") 302 that supplies and controls RF power. A suitable ESU is the Model 4810A ESU sold by Boston Scientific Corporation of Natick, Mass., which is capable of supplying and controlling power on an electrode-by-electrode basis. This is sometimes referred to as "multi-channel control." Typically, power to the probe 100 will typically be controlled as a function of the temperature at each electrode 108 in order to insure that tissue is coagulated without over-heating and causing coagulum and charring. With respect to temperature sensing at the electrodes 108, temperature is measured by the aforementioned temperatures sensors. Alternatively, in those instances where temperature sensors are not employed, the respective temperatures at each electrode 108 may be determined by measuring impedance at each electrode.

The ESU 302 transmits energy to the electrodes 108 by way of a cable 304. The cable 304 includes a connector 306, which may be connected to the electrical connector 132, a connector 308, which may be connected to a power output port 310 on the ESU 302. Tissue coagulation energy emitted by the electrodes 108 is returned to the ESU 302 through an indifferent electrode 312 that is externally attached to the skin of the patient with a patch, or one or more electrodes (not shown) that are positioned in the blood pool, and a cable 314. The cable 314 includes a connector 316 that may be connected to one of the power return ports 318 on the ESU 302. Preferably, the ESU power output port 310 and corresponding connector 308 have different configurations than the power return ports 318 and corresponding connector 316 order to prevent improper connections. The amount of power required to coagulate tissue ranges from 5 to 150 w.

It should be noted that the individual electrode control afforded by the ESU 302 facilitates the formation of lesions that do not extend all the way around the electrode supporting portion of the variable size structure 106. For example, curvilinear lesions may be formed within the left atrium (or other tissue structure) that only require the use of two of the electrodes 108.

Although the present inventions have been described in terms of the preferred embodiments above, numerous modifications and/or additions to the above-described preferred embodiments would be readily apparent to one skilled in the art. By way of example, but not limitation, the splines will not be identical in some implementations of the inventions. Moreover, the inventions include any and all combinations of the elements from the various embodiments disclosed in the specification, systems that comprise a power supply device (such as an ESU) in combination with any of the probes described above and/or claimed below, and apparatus including a sheath or other tubular member in combination with any of the probes described above and/or claimed below. It is intended that the scope of the present inventions extend to all such modifications and/or additions and that the scope of the present inventions is limited solely by the claims set forth below.

I claim:
1. A probe, comprising:
a probe body with a distal region defining a longitudinal axis;
a plurality of splines associated with the distal region of the probe body, each spline having a distally extending section, an arcuate operative element support section, a joint located between the distally extending support section and the arcuate operative element support section, and a distal end that is not connected to the other splines;

the joint in each spline being more flexible than the distally extending section and the operative element support section;

the arcuate operative element support sections together at least substantially forming a closed shape that is oriented transverse to the longitudinal axis in a first orientation and together forming a smaller closed shape that is oriented transverse to the longitudinal axis in a second orientation; and at least one operative element supported on at least one of the operative element support sections.

2. A probe as claimed in claim 1, wherein the probe body comprises a catheter body.

3. A probe as claimed in claim 1, wherein the closed shape comprises a substantially circular shape.

4. A probe as claimed in claim 1, wherein the closed shape is oriented substantially perpendicular to the longitudinal axis and is centered with respect to the longitudinal axis.

5. A probe as claimed in claim 1, wherein the splines are configured and positioned such that they do not overlap in the first orientation and overlap in the second orientation.

6. A probe as claimed in claim 1, wherein the splines are configured and positioned such that the distal end of each spline abuts an adjacent spline in the first orientation.

7. A probe as claimed in claim 1, wherein each spline comprises a core wire covered by an electrically non-conductive material.

8. A probe as claimed in claim 7, wherein the core wire comprises shape memory material.

9. A probe as claimed in claim 1, wherein the at least one operative element comprises an electrode.

10. A probe as claimed in claim 1, wherein at least one operative element is supported on each of the operative element support sections.

11. A probe as claimed in claim 1, wherein the arcuate electrode support sections each define an approximately 90 degree arc.

12. A probe as claimed in claim 1, wherein the plurality of splines are substantially identical to one another.

13. A probe, comprising:
a probe body with a distal region defining a longitudinal axis;
a plurality of splines associated with the distal region of the probe body, each spline having distally extending section, an arcuate operative element support section, and a distal end that is not connected to the other splines, and each spline including a core wire covered by an electrically non-conductive material, the core wire defining a first cross-sectional shape in the distally extending section and a second cross-sectional shape in the arcuate operative element support section that is different than the first cross-sectional shape;

the arcuate operative element support sections together at least substantially forming a closed shape that is oriented transverse to the longitudinal axis; and at least one operative element supported on at least one of the operative element support sections.

14. A probe as claimed in claim 13, wherein the probe body comprises a catheter body.

15. A probe as claimed in claim 13, wherein the core wire comprises shape memory material.

16. A probe as claimed in claim 13, wherein the first cross-sectional shape is substantially circular.

17. A probe as claimed in claim 13, wherein the second cross-sectional shape is substantially rectangular.

18. A probe as claimed in claim 13, wherein
the arcuate operative element support section has a bending direction; and
the second cross-sectional shape defines a long axis that is perpendicular to the bending direction and a short axis.

19. A probe as claimed in claim 13, further comprising:
a joint defining a third cross-sectional shape, which is different than the first cross-sectional shape, located between the distally extending support section and the arcuate operative element support section.

20. A probe as claimed in claim 13, wherein the arcuate operative element support sections together at least substantially form a closed shape in a first orientation and together form a smaller closed shape in a second orientation.

21. A probe as claimed in claim 20, wherein the splines are configured and positioned such that the distal end of each spline abuts an adjacent spline in the first orientation.

22. A probe as claimed in claim 20, wherein the splines are configured and positioned such that they do not overlap in the first orientation and overlap in the second orientation.

23. A probe as claimed in claim 13, wherein the closed shape comprises a substantially circular shape.

24. A probe as claimed in claim 13, wherein the closed shape is oriented substantially perpendicular to the longitudinal axis and is centered with respect to the longitudinal axis.

* * * * *